United States Patent
Hefner, Jr. et al.

(10) Patent No.: US 10,414,854 B2
(45) Date of Patent: Sep. 17, 2019

(54) EPOXY RESIN COMPOSITIONS

(71) Applicant: BLUE CUBE IP LLC, St. Louis, MO (US)

(72) Inventors: Robert E. Hefner, Jr., Midland, MI (US); Daryoosh Beigzadeh, Midland, MI (US); David J. Couling, Midland, MI (US); Robert W. Coyle, Midland, MI (US); David A. Carr, Midland, MI (US)

(73) Assignee: Blue Cube IP LLC, St. Louis, MO (US)

( * ) Notice: Subject to any disclaimer, the term of this patent is extended or adjusted under 35 U.S.C. 154(b) by 0 days.

(21) Appl. No.: 15/126,718

(22) PCT Filed: Feb. 26, 2015

(86) PCT No.: PCT/US2015/017699
§ 371 (c)(1),
(2) Date: Sep. 16, 2016

(87) PCT Pub. No.: WO2015/148040
PCT Pub. Date: Oct. 1, 2015

(65) Prior Publication Data
US 2017/0088663 A1 Mar. 30, 2017

Related U.S. Application Data

(60) Provisional application No. 61/969,290, filed on Mar. 24, 2014.

(51) Int. Cl.
*C08G 59/04* (2006.01)
*C07D 301/28* (2006.01)

(52) U.S. Cl.
CPC ............ *C08G 59/04* (2013.01); *C07D 301/28* (2013.01)

(58) Field of Classification Search
CPC ....... C07C 37/20; C07C 39/17; C07C 261/02; C07C 2101/14
See application file for complete search history.

(56) References Cited

U.S. PATENT DOCUMENTS

2004/0202864 A1* 10/2004 Murata .................. C08G 59/04
428/413
2013/0178601 A1* 7/2013 Hefner, Jr. ............ C07D 301/28
528/406

FOREIGN PATENT DOCUMENTS

WO 2012/044442 4/2012

OTHER PUBLICATIONS

PCT/US2015/017699 International Search Report dated Jul. 13, 2015.

* cited by examiner

*Primary Examiner* — Shane Fang
(74) *Attorney, Agent, or Firm* — Husch Blackwell LLP

(57) ABSTRACT

A process for preparing an aliphatic or cycloaliphatic epoxy resin composition including the steps of: (I) reacting a mixture of the following components: (a) an aliphatic or cycloaliphatic hydroxyl-containing material, (b) an epihalohydrin, (c) a stoichiometric excess of a base compound or basic acting substance, (d) a catalyst, and (e) optionally, a solvent; wherein the reacting step (I) is carried out under reaction conditions sufficient to form a crude aliphatic or cycloaliphatic epoxy resin composition product in the resultant reaction mixture; (II) neutralizing the resultant reaction mixture of step (I) containing the crude aliphatic or cycloaliphatic epoxy resin composition product with a phosphate neutralizing agent sufficient to partially neutralize the base or basic acting substance and to form a neutralized fluid medium containing aliphatic or cycloaliphatic epoxy resin composition product; (III) removing at least a portion of unreacted epihalohydrin from the reaction mixture of step (II); and (IV) subjecting the reaction mixture of step (III) above to a separation process to recover the aliphatic or cycloaliphatic epoxy resin composition product from the neutralized fluid medium; wherein the aliphatic or cycloaliphatic epoxy resin composition product yield is greater than about 70 percent.

14 Claims, No Drawings

EPOXY RESIN COMPOSITIONS

FIELD

The present invention is related to a process for making an aliphatic and cycloaliphatic epoxy resin composition with several advantageous properties including for example a high content of cyclohexanedimethanol diglycidyl ether or epoxy resin of cyclohexanedimethanol, a low content of monoglycidyl ether, a low content of oligomers, and a low content of hydrolyzable chlorides.

BACKGROUND

The chemistry and processes used for manufacturing aliphatic and cycloaliphatic epoxy resins via epoxidation of aliphatic and cycloaliphatic hydroxyl containing materials (e.g., cyclohexanedimethanol [CHDM]) using an epihalohydrin are difficult, if not impossible, to drive to full conversion; and such processes produce significant quantities of undesirable partially epoxidized products, such as, for example, cyclohexanedimethanol monoglycidyl ether (CHDM-MGE) (as much as 2 weight percent [wt %] to 20 wt % of the epoxy resin composition), as well as oligomeric co-products (as much as 25-40 wt % of the epoxy resin composition).

It has been found that the presence of residual undesirable components, such as CHDM-MGE, in the aliphatic and cycloaliphatic epoxy (ACE) resin product such as a diglycidyl ether (DGE) or epoxy resin of cyclohexanedimethanol (CHDM-DGE) product, is deleterious to the acid resistance of coatings prepared therefrom. Chain termination caused by the mono-functionality of the CHDM-MGE may also result in reduction of mechanical properties, glass transition temperature (Tg) and reactivity with curing agents. Heretofore, various methods, such as, for example, fractional vacuum distillation, have been used for the partial removal of CHDM-MGE from CHDM-DGE product; however, such known methods used for removal of CHDM-MGE may also remove excessive CHDM-DGE leading to a resulting ACE resin product with an elevated viscosity and a reduced reactivity with curing agents. Thus, to alleviate the aforementioned deficiencies it would be highly desirable to be able to produce an ACE resin which specifically contains low CHDM-MGE (e.g., less than [<] about 6 wt %) while maintaining a high level of CHDM-DGE (e.g., greater than [>] about 80 wt %) with the balance as oligomers.

Various ACE resin products are known to be produced with processes of the prior art including: (1) high purity DGEs of ACE resins, (2) ACE resins produced using non-Lewis acid catalyzed processes, (3) low monoglycidyl ether (MGE) ACE resins, (4) advanced DGEs of ACE resins (containing residual glycidyl ether functionality), (5) partially or completely hydrolyzed aliphatic or cycloaliphatic DGEs, and (6) mixtures of one or more epoxy resins described in (1)-(5) above.

For example, processes for preparing ACE resin products of (1)-(4) above are disclosed, for example, in WO 2012/044442A1; WO 2012/044443A1; WO 2012/044455A1; WO 2012/044458A1; WO 2012/044490A1; WO 2012/047420A2; WO 2012/050688A2; and WO 2012/050777A1; all of which are incorporated herein by reference.

The known processes described above have several drawbacks which make the processes, and the products produced by such processes, undesirable for an industrial scale process for mass producing large quantities of ACE resins. For instance, the known processes use catalysts, and in some instances solvents, that must be removed from the ACE product before the resin can be used in a subsequent operation. In addition, the known processes for producing (5) above produce large quantities of bis-α-glycol species in the epoxy resin in addition to mono-α-glycol species. Such bis-α-glycol species present in the epoxy resin have no curable epoxide groups, and thus, the bis-α-glycol species may: (1) depress Tg of articles (thermosets) made from the epoxy resin containing such species; (2) migrate to the surface of the thermoset causing softness or tackiness; and/or (3) depress mechanical properties such as modulus.

It is desired to provide aliphatic or cycloaliphatic DGEs or epoxy resins particularly, for example, CHDM-DGE, having significantly enhanced properties, such as a low content of CHDM-MGE and/or a low content of hydrolyzable chloride, compared to the above currently known CHDM-DGE resins.

SUMMARY

The present invention desirably addresses some or all of the aforementioned deficiencies of the prior art. Accordingly, one aspect of the present invention is directed to a novel process for producing an ACE resin composition. The ACE resin composition prepared by the process of the present invention has several beneficial properties including for example, low viscosity, low MGE, high average (curable) epoxide and improved shelf life. With respect to shelf life, isolated aliphatic and cycloaliphatic MGEs are prone to slow polymerization at room temperature (about 25° C.) causing an increase in viscosity, a reduction in epoxide functionality available for cure, and ultimately, gelation of the isolated aliphatic and cycloaliphatic MGEs.

Advantageously, an ACE resin composition without some or all of the above deficiencies can be prepared by the process of the present invention; and the ACE resin composition of the present invention can be used to prepare a curable composition. The curable composition, in turn, can be used to prepare a cured product from the curable composition.

In general, one embodiment of the present invention includes a process for producing an ACE resin, particularly a CHDM epoxy resin including for example, the steps of:
(I) reacting a mixture of the following components:
  (a) an aliphatic or cycloaliphatic hydroxyl-containing material,
  (b) an epihalohydrin,
  (c) a stoichiometric excess of a base compound,
  (d) a catalyst, and
  (e) optionally, a solvent; wherein the reacting step is carried out under reaction conditions sufficient to form an ACE resin composition product in the resultant reaction mixture;
(II) neutralizing the resultant reaction mixture containing the ACE resin composition product with a phosphate neutralizing agent sufficient to partially neutralize the basic acting substance and to form a neutralized fluid medium containing the ACE resin composition product;
(III) removing at least a part or portion of unreacted epihalohydrin from the reaction mixture of step (II); and
(IV) subjecting the reaction mixture of step (III) above to a separation process to recover the ACE resin composition product from the neutralized fluid medium.

Some other advantages of employing the process for preparing the ACE resin composition of the present invention include for example, when using the present process it is not necessary to change the conventional process equipment and unit operations of the process to produce and recover the epoxy resin product. In addition, the present process does not require the use of additional components such as solvent(s) or other additives. Also, the present process is generally performed under mild conditions, such as at a temperature of from about 25° C. to about 60° C. for step (I).

In other embodiments, the ACE resin composition produced by the process of the present invention can be used to prepare thermosettable (curable) compositions and cured thermosets therefrom.

DETAILED DESCRIPTION

One broad embodiment of the present invention comprises a process for producing an ACE resin composition.

For example, one embodiment of the present invention includes a process for producing an ACE resin, for example a CHDM epoxy resin, by carrying out the steps of:

Step (I): reacting a mixture of the following components:
(a) an aliphatic or cycloaliphatic hydroxyl-containing material,
(b) an epihalohydrin,
(c) a stoichiometric excess of a base compound or basic acting substance,
(d) a catalyst, and
(e) optionally, a solvent; wherein the reacting step is carried out under reaction conditions sufficient to form an ACE resin composition product in the resultant reaction mixture;

Step (II): neutralizing the resultant reaction mixture containing the ACE resin composition product with a phosphate neutralizing agent sufficient to partially neutralize the basic acting substance and to form a neutralized fluid medium containing the ACE resin composition product; and Step (III): removing at least a portion of unreacted epihalohydrin from the reaction mixture of step (II); and Step (IV): subjecting the reaction mixture of step (III) above to a separation process to recover the ACE resin composition product from the neutralized fluid medium.

The first step, in accordance with the process of the present invention for making the ACE resin compositions, can be an anhydrous epoxidation of aliphatic or cycloaliphatic hydroxyl-containing compounds in which water is azeotropically removed from the reaction. This process step is also referred to as "azeotropic epoxidation".

For example, the azeotropic epoxidation process can be carried out by preparing a mixture of: (a) an aliphatic or cycloaliphatic hydroxyl-containing material; (b) an epihalohydrin; (c) a stoichiometric excess of a base (based on moles of hydroxyl groups in starting material, component (a)); (d) a catalyst such as a non-Lewis acid catalyst; and optionally, (e) a solvent. In the process, a controlled amount of (c) a base or basic acting substance such as an aqueous base solution is controllably added to the stirred mixture of: (a) an aliphatic or cycloaliphatic hydroxyl containing material; (b) an epihalohydrin; and (d) a non-Lewis acid catalyst; and such controlled addition can be performed with continuous vacuum distillation of an epihalohydrin-water azeotrope. The water fraction from the distilled azeotrope can then be removed, and the recovered epihalohydrin can be recycled back into the reaction.

By stoichiometric excess of base, component (c) described above, it is meant herein that the base is used, generally, in an amount in the range of from about 1 to about 2 molar equivalents of base to the hydroxyl groups in component (a) in one embodiment; from about 1.05 to about 2.0 molar equivalents of base to the hydroxyl groups in component (a) in another embodiment; from about 1.1 to about 1.9 molar equivalents of base to the hydroxyl groups in component (a) in still another embodiment; and from about 1.2 to about 1.6 molar equivalents of base to the hydroxyl groups in component (a) in yet another embodiment.

An ACE resin composition is formed by the above azeotropic epoxidation step of the present process. The epihalohydrin may additionally serve as a solvent in the azeotropic epoxidation process step. However, a solvent other than, or in addition to, the excess stoichiometric epihalohydrin may optionally be used as a solvent in the present azeotropic epoxidation process step.

The epoxidation process step of the present invention may be carried out under various process conditions. For example, the temperature used in the epoxidation process is generally from about 20° C. to about 90° C. in one embodiment, from about 25° C. to about 60° C. in another embodiment, and from about 30° C. to about 50° C. in still another embodiment. The pressure used in the epoxidation process is generally from about 1333 Pa (10 mm Hg) vacuum to about 700 kPa (100 psia) in one embodiment, from about 4000 Pa (30 mm Hg) vacuum to about 350 kPa (50 psia) in another embodiment, and from about 5333 Pa (40 mm Hg) vacuum to about atmospheric pressure (e.g., 760 mm Hg) in still another embodiment. The time for completion of the epoxidation process is generally from about 1 hour to about 120 hours in one embodiment, from about 2 hours to about 72 hours in another embodiment, and from about 3 hours to about 24 hours in still another embodiment.

Any aliphatic or cycloaliphatic hydroxyl-containing reactant may be employed in the epoxidation process to produce the ACE resin. Some representative classes of aliphatic and/or cycloaliphatic hydroxyl-containing materials which may be employed in the epoxidation process include for example any one or more of the following compounds: cyclohexanedialkanols and cyclohexenedialkanols such as for example UNOXOL™ Diol (a mixture of cis- and trans-1,3- and 1,4-cyclohexanedimethanol); 1,4-cyclohexanedimethanol; and other aliphatic and cycloaliphatic hydroxyl-containing compounds described in pages 9 to 15 of WO2012047420(A), incorporated herein by reference.

The epihalohydrin, the base or basic acting substance component, the catalyst such as a non-Lewis acid catalyst, and the optional solvent useful in the epoxidation process step may be selected from one or more of the same components as described in page 15 to page 18 of WO2012/047420, incorporated herein by reference.

One preferred embodiment of the present invention includes, for example, a process for the production of a CHDM epoxy resin. Generally, CHDM epoxy resin is the product of reaction of CHDM with epichlorohydrin and sodium hydroxide in the presence of a catalyst such as a non-Lewis acid catalyst. Sodium chloride and water are by-products of the intended reaction for producing CHDM epoxy resin. The epoxidation reaction step of the present process can be ideally illustrated by Scheme I as follows:

Scheme I

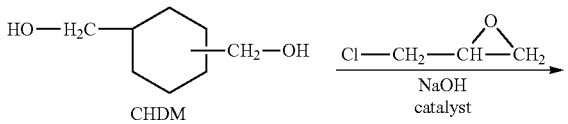

-continued

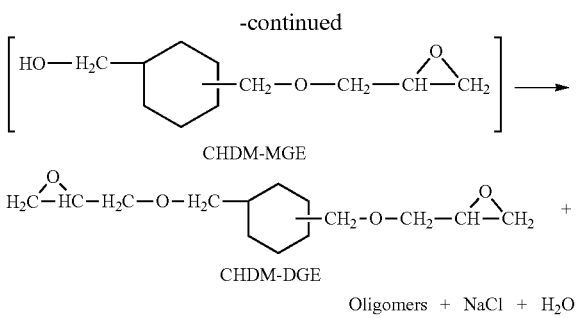

Oligomers + NaCl + H₂O

The present invention process includes a step (II) of removing residual alkalinity from the epoxy resin product by employing a neutralizing agent and adjusting the stoichiometry of the neutralizing agent to form the partially neutralized ACE resin product.

In accordance with the present invention, the ACE resin product from the azeotropic epoxidation reaction described above is treated with a neutralizing agent in an amount and at reaction conditions sufficient to produce the desired amount of ACE resin product while removing at least a portion or part of the alkalinity from the reaction mixture containing the ACE resin product. For example, once the ACE resin product, particularly a CHDM-epoxy resin, is produced in the epoxidation step, the resultant ACE resin can be neutralized using a neutralizing agent, such as an aqueous solution of sodium dihydrogen phosphate, to neutralize alkaline salts.

Sodium dihydrogen phosphate (monobasic sodium phosphate), potassium dihydrogen phosphate, phosphoric acid, and mixtures thereof, are examples of the neutralizing agent which can be employed in the present invention to remove excess alkaline agent, such as sodium hydroxide used in the epoxidation process. Sodium dihydrogen phosphate can be conveniently prepared and used as an aqueous solution, such as a solution containing about 13 wt % neutralizing agent.

In the process of the present invention, a less than stoichiometric equivalent of a neutralizing agent ("partial neutralization") may be used for removal of undesirable alkalinity from the ACE resin product. For full neutralization, a stoichiometric equivalent is required to fully neutralize the alkalinity. The amount of the neutralizing agent used for partial neutralization varies depending on the structure of the neutralizing agent, the amount of excess basic acting substance or base used in the epoxidation, the amount of residual alkalinity present in the epoxy resin product, the amount of hydrolysis occurring, the planned reaction time for the neutralizing agent, the neutralization reaction temperature, the epoxy resin, and the like.

Generally, for complete neutralization, the amount of neutralizing agent used in the process is calculated based on the total amount of the excess base from the reaction step. In one preferred embodiment, the present invention is directed to partial neutralization. "Partial neutralization" herein means neutralizing less than stoichiometric excess of the base used in the epoxidation step. The amount of neutralizing agent needed for partial neutralization is less than 100% of the stoichiometric excess of the base utilized during the reaction step; and the amount of neutralizing agent is reported herein as a certain percent neutralization. For example, the amount of neutralizing agent used in the present process is generally from about 1 percent (%) to about 99% of the stoichiometric excess of base utilized during the epoxidation reaction step in one embodiment, from about 2% to about 90% in another embodiment, from about 5% to about 80% in still another embodiment, from about 10% to about 70% in yet another embodiment, from about 10% to about 50% in even still another embodiment, and from about 20% to about 50% of the stoichiometric excess of base utilized during the epoxidation reaction step in even yet another embodiment. Partial neutralization has been found to be particularly beneficial in that the use of neutralizing agent is conserved, aqueous salt waste production is minimized and ACE resin product which meets desired specifications is still obtained. Partial neutralization of CHDM epoxy resins in the range of from about 20% to about 90% neutralization has been found to be particularly beneficial.

Not carrying out the neutralization step in accordance with the present process can result in the formation of undesirable insoluble polymeric material, which in turn, can result in unwanted waste and a reduction in product yield. The formation of undesirable insoluble polymeric material can also significantly retard or inhibit phase separation during the wash steps which can complicate the subsequent steps in the present process and which can further reduce the overall product yield. On the other hand, it is also important to avoid over-neutralization in the present process because further reaction can occur which causes hydrolysis of epoxide groups in the ACE resin product and thus forms a completely different epoxy resin composition (partially hydrolyzed ACE resin product) when formation of the (non-hydrolyzed) ACE resin product was intended. "Over-neutralization" of the ACE resin in the process can occur, for example, by adding a neutralizing agent in excess of that needed to consume the remaining alkalinity from the epoxidation step. Although excess neutralizing agent and hydrolysis reaction product of the neutralizing agent can be substantially removed from the partially hydrolyzed ACE resin, for example, by intensive water washing or by post treatment with a base and, optionally, catalyst, followed by water washing, partial neutralization is still advantageous because partial neutralization avoids the aforementioned problems including generation of additional aqueous waste and loss of ACE resin product.

In addition, by carrying out the partial neutralization step in the process of the present invention, beneficial results occur such as a high isolated product yield can be produced, the subsequent steps of the process after partial neutralization can be simplified, and the cost of using unnecessary quantities of neutralizing agent can be avoided.

An alternative embodiment to determining the degree of neutralization, i.e., whether neutralization is complete or partial, can be carried out by adding a sufficient amount of neutralizing agent to the reaction mixture to achieve a desired pH of the mixture diluted with water. In this embodiment, the neutralizing agent may be added in increments followed by pH analysis. For example, after an increment of neutralizing agent is added to the reaction mixture, a predetermined sample of the neutralized mixture (epoxy resin product and the neutralizing agent mixture) is obtained and diluted with a predetermined amount of water. The pH of the water diluted epoxy resin product and the neutralizing agent mixture is then determined. Partial neutralization results when the pH values of the water diluted epoxy resin product is above about 7 in one embodiment and from about 8 to about 13 in another embodiment.

As described above, the neutralizing step can be carried out to remove alkalinity from the crude ACE resin product resulting from the epoxidation step described above. Optionally, one or more solvents can be added to the crude ACE resin product before or after the neutralizing agent is used. Treatment with neutralizing agent can be done using an amount of neutralizing agent and reaction conditions which produce the desired amount of reduction of alkalinity in the ACE resin product in the presence or in the absence of a solvent.

Alternatively, after completion of addition of the aqueous basic acting substance during the epoxidation step and any post reaction step, the crude ACE resin product resulting from the epoxidation step described above may be subjected to further distillation conditions to substantially remove unreacted epihalohydrin along with co-produced lights. The neutralizing step can be carried out after the crude epoxy resin product from the epoxidation step is first stripped to remove a part or all of the unreacted epichlorohydrin present in the reaction mixture. Generally, the final concentration of epichlorohydrin in the ACE resin product at the end of the stripping process can be, for example, <about 300 ppm.

In other embodiments, the neutralizing step can be carried out either before or after a water washing step of the crude ACE resin product resulting from the epoxidation step described above. In a preferred embodiment, the present process includes carrying out the neutralizing step before the ACE resin composition product resulting from the epoxidation step is passed through a water washing step.

In still another embodiment, the neutralizing step can be carried out after a water washing step of the crude epoxy resin and after a stripping step of the crude epoxy resin to remove all or a part of the unreacted epichlorohydrin.

In yet another embodiment, the neutralizing step can be carried out after a water washing step of the crude epoxy resin, after a stripping step of the crude epoxy resin to remove all or a part of the unreacted epichlorohydrin, and after a step of combining the resultant water-washed, epichlorohydrin-stripped crude epoxy resin with a solvent, such as toluene.

In a preferred embodiment, the step (III) of removing at least a portion of unreacted epihalohydrin, such as epichlorohydrin, from the reaction mixture after the reaction step (I) and the neutralization step (II) can be carried out after the neutralization step (II) and by conventional means. Unreacted epichlorohydrin can be removed from the reaction mixture, for example, by a conventional stripping process, through known combinations of temperature and vacuum. For example, the temperature of stripping can be from about 40° C. to about 130° C.; and the stripping pressure can be absolute pressure at a range of from about 2,000 Pa to about 100,000 Pa. The epichlorohydrin removed from the reaction mixture can be used in subsequent epoxidations to prepare the same or other products. Typically, the combination of high temperature and excess base during the stripping step results in the formation of insoluble polymeric material. In the present invention process, the use of the partial neutralization step advantageously minimizes the formation of these insoluble polymeric materials.

As described above, the partial neutralization step (II) is carried out to partially neutralize the base or basic acting substance and to form a neutralized fluid medium containing ACE resin product; and the partial neutralization step is carried out to minimize the amount of undesirable insoluble polymeric material formed. Ideally, after the partial neutralization and stripping steps, no insoluble polymeric material is formed or present in the neutralized fluid medium because formation of insoluble polymeric material reduces the yield of product. In general however, some amount of insoluble polymeric material can be formed during the process of the present invention. For example, the amount of insoluble polymeric material formed can be generally less than about 10 wt % in one embodiment, from about 0.01 wt % to about 8 wt % in another embodiment, and from about 0.01 wt % to about 5 wt % in still another embodiment, based on the final epoxy resin product recovered.

After step (III) of removing at least a portion of unreacted epihalohydrin, from the reaction mixture, the present invention process includes a separation and recovery step (IV) by subjecting the reaction mixture of step (III) above to a separation process to recover the ACE resin composition product from the neutralized fluid medium with the objective of obtaining the greatest yield of the ACE resin composition product. However, as aforementioned, formation of undesirable insoluble polymeric material results in unwanted waste, and significantly retards or inhibits the phase separation during the separation step (IV) of the present process and any wash steps if used; the formation of undesirable insoluble polymeric material complicates the subsequent steps in the present process, which further reduces the overall yield of the isolated desirable product.

Generally, the overall yield of the isolated desirable product can be greater than about 70% in one embodiment, greater than about 75% in another embodiment, greater than about 80% in still another embodiment, greater than about 85% in yet another embodiment, greater than about 90% in even still another embodiment, and greater than about 95% in even yet another embodiment; and ideally, the overall yield of the isolated desirable product can be up to 100%. In another embodiment, the overall yield of the isolated desirable product can be from about 70% to about 100%, from about 80% to about 98% in still another embodiment, and from about 85% to about 95% in yet another embodiment. The above product yield percentages are defined herein as percentages based on the theoretical yield calculated from stoichiometry of the reaction step (I).

Other optional processing steps may be carried out, in addition to steps (I)-(IV) of the present invention process described above, including for example, one or more washing steps; one or more treating steps to remove hydrolyzable chloride when present in the reaction mixture; one or more solvent stripping steps when solvent is used in the process; one or more distillation processing steps to remove unreacted epihalohydrin and/or co-produced lights produced during the epoxidation step; and/or one or more centrifugation or filtration steps to remove solid materials from the resulting liquid ACE resin product.

Any conventional equipment known to those skilled artisans can be used to carry out the manufacturing process of the present invention. For example, the equipment can include epoxidation reactor vessels; liquid/liquid separation vessels; evaporation vessels such as rotary evaporators; and fractionation vessels such as distillation apparatus; which are known in the art.

Conventional processes or series of processes for isolating and recovering the ACE resin may be employed herein. For example, methods such as vacuum distillation including rotary evaporation, fractional vacuum distillation, short path distillation, packed column distillation, spinning band column distillation, falling film distillation, wiped film distillation, steam distillation, filtration including vacuum filtration, gravity filtration, nanofiltration, microfiltration and ultrafiltration, membrane separations including pervaporation and vapor permeation, centrifugation, water washing or extraction, solvent extraction, supercritical fluid extraction, decantation, column chromatography, electrostatic coalescence, adsorption, and other known fractionation and separation processing methods and the like may be employed.

The ACE resin product of the present invention can be used in various applications such as for example to form curable resin formulations/compositions and thermosets made from such curable compositions. For example, the ACE resin product can be mixed with a curing agent and/or a curing catalyst for making a thermosettable resin; and the thermosettable resin, in turn, can be partially cured (B-staged) to form a B-stage material or completely cured to form a thermoset article. The ACE resin product can also be blended with conventional epoxy resins and cured. Conventional curing agents and additives (in addition to the ACE resin and curing agent) known to the skilled artisan can be included in the curable composition (e.g., a curing catalyst and other additives) to prepare the curable compositions for various applications. The preparation of the curable formulation, and/or any of the steps thereof, may be a batch or a continuous process. The mixing equipment used in the process may be any vessel and ancillary equipment well known to those skilled in the art of preparing curable compositions.

Also, conventional curing reaction conditions known to the skilled artisan, including for example temperatures sufficient to cure the composition (e.g., −10° C. to about 300° C.), and conventional processes/equipment, can be used to cure the curable compositions to form a cured thermoset. For example, the process to produce the cured ACE resin products may be performed by gravity casting, vacuum casting, automatic pressure gelation (APG), vacuum pressure gelation (VPG), infusion, filament winding, lay up injection, transfer molding, prepregging, coating, such as roller coating, dip coating, spray coating and brush coating, and the like.

The ACE resin/curing agent curable compositions of the present invention may be used to prepare cured thermosets or articles such as coatings, adhesives, films, foams, laminates, prepregs and composites that exhibit a combination and balance of advantageous properties including for example processability, Tg, mechanical performance and physical properties.

In one embodiment, an ACE resin having a low content of CHDM-MGE can be preferably used for preparing coatings such as in the field of weatherable coatings wherein the cured aliphatic and cycloaliphatic thermoset epoxy resin matrices of the present invention can advantageously exhibit reduced yellowing and chalking upon weathering, typically observed with conventional aromatic thermoset epoxy resin matrices.

EXAMPLES

The following Examples and Comparative Examples further illustrate the present invention in detail but are not to be construed to limit the scope thereof. All parts and percentages are by weight unless otherwise indicated.

The following standard abbreviations are used in the Examples and Comparative Examples: "CHDM" stands for cyclohexanedimethanol, "MGE" stands for monoglycidyl ethers, DGE stands for "diglycidyl ethers", "Epi" stands for epichlorohydrin; "GC" stands for gas chromatography (chromatographic), "EEW" stands for epoxide equivalent weight, "DI" stands for deionized, "eq" stands for equivalent(s); "wt" stands for weight(s), "vol" stands for volume(s), "min" stands for minute(s), "hr" stands for hour(s), "mg" stands for milligrams, "g" stands for gram(s), "µL" stands for microliter(s), "mL" stands for milliliter(s), "L" stands for liter(s), "µm" stands for micrometer(s), "mm" stands for millimeter(s), "m" stands for meter(s), and "mPa-s" stands for millipascals-seconds.

In the following Examples and Comparative Examples, standard analytical equipment and methods are used such as for example, the following:

Viscosity and Density

Viscosity and density were determined on Stabinger Viscometer (Model SVM 3000, Anton Paar) at 25° C.

Percent Epoxide/Epoxide Equivalent Weight Analysis

A standard titration method is described in Jay, R. R., "Direct Titration of Epoxy Compounds and Aziridines", Analytical Chemistry, 36, 3, 667-668 (March, 1964). The method described in the above reference was slightly modified and used to determine percent epoxide in the various epoxy resins disclosed herein. The general method used in the present examples included the following: a carefully weighed sample (sample weight ranges from 0.17 g to 0.25 g) was dissolved in dichloromethane (15 mL) followed by the addition of tetraethylammonium bromide solution in acetic acid (15 mL). The resultant solution, treated with 3 drops of crystal violet indicator (0.1% wt/vol in acetic acid), was titrated with 0.1 N perchloric acid in acetic acid on a Metrohm 665 Dosimat titrator (Brinkmann). Titration of a blank consisting of dichloromethane (15 mL) and tetraethylammonium bromide solution in acetic acid (15 mL) provided correction for solvent background. Percent epoxide and EEW were calculated using the following equations:

$$\% \text{ Epoxide} = \frac{[(\text{mL titrated sample}) - (\text{mL titrated blank})](0.4303)}{(\text{g sample titrated})}$$

$$EEW = \frac{4303}{\% \text{ epoxide}}$$

Gas Chromatographic Analysis

In a general method of GC analysis, an Agilent 6890 gas chromatograph was employed using a DB-5 capillary column (30 m by 0.32 mm with a 0.25 µm film thickness, Agilent). Injector inlet temperature was maintained at 300° C. and the flame ionization detector was maintained at 340° C. Split injection was used with a split ratio of 100:1. Helium carrier gas flow through the column was maintained at 4 mL per min. For the analyses of the epoxy resins an initial 50° C. oven temperature for 1 min with subsequent heating at 12° C. per min to a final temperature of 335° C. with final hold of 15 min, was employed. Internal standard calibration was used for quantification purposes.

Samples for GC analysis were prepared by the addition of a 100 mg aliquot of the filtered product (filtered through a 0.2 μm syringe filter) from the epoxidation to a 20 mL vial. It was followed by addition of 50 mg of cyclohexanone, as internal standard and addition of 4.7 g of acetonitrile, as solvent. After shaking to mix, a portion of the solution in acetonitrile was loaded into a standard GC vial (made by Agilent). Using the GC's auto sampler, 1 μL of the solution was injected into the inlet.

Example 1

Part A: Epoxidation Reaction

Reaction of CHDM with epichlorohydrin was carried out in a 2 L reactor equipped with an electrical heater, an agitation system, a condenser, a decanter with a separatory funnel, a vacuum pump and a pressure controller. CHDM, 180.6 g, and epichlorohydrin, 579.05 g, were loaded into the reactor at room temperature (about 25° C.). The reactor was then heated to 40° C. Benzyltriethylammonium chloride, 29 g, was then added as a 60% solution in water which was then added to the reactor. The internal pressure of the reactor was reduced using the vacuum pump and pressure controller to the point that kept the reactor contents at 40° C. while the contents were boiling. The reactor was kept under vacuum and heat for 15 min in order to remove the water that had been introduced to the reactor by the addition of the aqueous catalyst. At this point, using a pump, a 50% solution of NaOH in water, 240.3 g, was fed to the reactor over a period of 11 hr. As reaction proceeded the boiling point of the contents changed, due to the formation of the product and decrease in epichlorohydrin concentration through reaction, and lower pressures were required. Table I describes the variations in reactor temperature and pressure through the course of the reaction. In Table I, "Ti" is the internal temperature of the reactor and "Tj" is the jacket temperature of the reactor.

TABLE I

Variations in Reactor Temperature and Pressure

| Time (min) | Ti (° C.) | Tj (° C.) | Absolute Pressure (Pa) |
|---|---|---|---|
| 0 | 40 | 76 | 6,000 |
| 19 | 40 | 76 | 5,500 |
| 47 | 40 | 77 | 5,300 |
| 67 | 40 | 80 | 5,300 |
| 88 | 40 | 77 | 5,100 |

TABLE I-continued

Variations in Reactor Temperature and Pressure

| Time (min) | Ti (° C.) | Tj (° C.) | Absolute Pressure (Pa) |
|---|---|---|---|
| 108 | 40 | 78 | 5,000 |
| 126 | 40 | 79 | 5,000 |
| 153 | 40 | 79 | 4,900 |
| 174 | 40 | 77 | 5,000 |
| 198 | 40 | 77 | 4,900 |
| 231 | 40 | 78 | 4,900 |
| 258 | 40 | 77 | 5,000 |
| 268 | 40 | 79 | 4,600 |
| 287 | 40 | 76 | 4,600 |
| 306 | 40 | 79 | 4,800 |
| 331 | 40 | 76 | 4,600 |
| 357 | 40 | 79 | 4,600 |
| 375 | 40 | 77 | 4,400 |
| 399 | 40 | 80 | 4,400 |
| 427 | 40 | 76 | 4,400 |
| 443 | 40 | 78 | 4,200 |
| 487 | 40 | 77 | 4,200 |
| 510 | 40 | 79 | 4,300 |
| 531 | 40 | 79 | 4,100 |
| 546 | 40 | 77 | 4,000 |
| 577 | 40 | 78 | 4,000 |
| 606 | 40 | 76 | 3,900 |
| 633 | 40 | 79 | 3,800 |
| 657 | 40 | 79 | 3,800 |
| 668 | 40 | 78 | 3,600 |

Hourly samples were taken to check for water content, using Karl Fischer titration. Water content data is presented in Table II.

TABLE II

Variations in Water Content with Reaction Time

| Reaction Time (min) | Water Content (wt %) |
|---|---|
| 60 | 0.63 |
| 128 | 0.53 |
| 180 | 0.50 |
| 240 | 0.49 |
| 300 | 0.45 |
| 360 | 0.35 |
| 420 | 0.33 |
| 480 | 0.20 |
| 540 | 0.22 |
| 600 | 0.22 |
| 640 | 0.20 |

At the completion of the caustic feed, the reactor contents were kept at 40° C. under vacuum for 30 min in order to complete the epoxidation reaction. Sample was taken at the end of digestion time and analyzed with gas chromatography in order to determine the concentration of main components in the organic phase. The results are described in Table III.

TABLE III

Concentrations (wt %) of Main Components of the Organic Phase

| Reaction Time (min) | NaOH:CHDM-OH Eq. Ratio Added | Epichlorohydrin (wt %) | CHDM (wt %) | CHDM-MGE (wt %) | CHDM-DGE (wt %) | Lights plus Oligomers (wt % by difference) |
|---|---|---|---|---|---|---|
| 675 | 1.2 | 53.49 | 0.02 | 1.73 | 35.84 | 8.91 |

Part B: Neutralization

At the completion of the reaction step described above in Part A, the contents of the reactor were neutralized by adding 193.7 g of a 13 wt % solution of monobasic sodium phosphate to the reaction mixture in the reactor (Table VI). The reactor contents were then heated under vacuum to strip epichlorohydrin.

Part C: Epichlorohydrin Strip

Epichlorohydrin was stripped by applying heat and vacuum to the reactor contents after the neutralization step in Part B. Temperature and pressure data are presented in Table IV.

TABLE IV

Variations in Reactor Temperature and Pressure

| Time (min) | Ti (° C.) | Tj (° C.) | Absolute Pressure (Pa) |
|---|---|---|---|
| 0 | 46 | 92 | 120,000 |
| 15 | 48 | 90 | 120,000 |
| 25 | 49 | 102 | 120,000 |
| 85 | 52 | 106 | 120,000 |
| 103 | 53 | 105 | 120,000 |
| 145 | 56 | 102 | 120,000 |
| 170 | 57 | 102 | 120,000 |
| 190 | 57 | 104 | 120,000 |
| 204 | 58 | 103 | 120,000 |
| 217 | 59 | 122 | 120,000 |
| 223 | 60 | 141 | 120,000 |
| 230 | 54 | 141 | 8,000 |
| 247 | 62 | 141 | 8,000 |
| 265 | 81 | 140 | 5,000 |
| 278 | 105 | 142 | 4,000 |
| 285 | 115 | 142 | 3,000 |
| 294 | 122 | 142 | 3,000 |
| 310 | 123 | 135 | 3,000 |

Gas chromatographic analysis of the reactor contents at the end of the stripping step indicates that the epichlorohydrin level was reduced to about 0.5 wt %.

Part D: Washes/Phase Separation

After the epichlorohydrin stripping in Part C, the reactor contents were cooled to below 30° C. and 584 g of DI water was added to the reactor and mixed for 15 min. The reactor contents were then transferred into a separatory funnel. Phase separation was quick, such that in less than 10 min the interface between the organic and water phases was clearly observed. After 30 min, the water phase was removed and organic phase was kept in the funnel. The weight of the organic phase collected in the funnel was 350 g. Water, 150.7 g, and toluene, 759.7 g, were added to further wash the sample. Phase separation was slow with small amount of insoluble material observed at the interface. The contents in the funnel were allowed to phase separate for 2 hr. The water phase was removed and the organic phase kept in the funnel. The polymeric insoluble phase, collected at the interface of water and organic phases, was collected and dried. The weight of the dried polymeric insoluble material was 1.1 g (Table VI).

Part E: Post Treatment to Reduce Hydrolyzable Chloride Content

The hydrolyzable chloride content of the organic phase was measured to be 16,576 ppm, based on the analysis of an aliquot of the neat ACE resin product. The organic phase, 1026 g, was transferred back into the reactor for post treatment. About 15 g of NaOH solution (50%) and 1 g of benzyltriethylammonium chloride solution (60%) were added to the reactor. The reactor contents were then heated to 80° C. and maintained at that temperature for 2 hr. The reactor was then cooled and a sample of the reactor contents was removed from the reactor.

The hydrolyzable chloride content of the organic phase after the above treatment was measured and found to be reduced to 783 ppm based on the analysis of an aliquot of the neat ACE resin product. About 174.9 g of water was added to the reactor contents followed by blending for 10 min. The reactor contents were transferred to a separatory funnel. About 174.6 g of water phase was removed from the funnel.

The organic phase was transferred from the funnel to the reactor for another round of post treatment ("second treatment"). About 2 g of NaOH solution (50%) and 1 g of benzyltriethylammonium chloride solution (60%) were added to the reactor. The reactor contents were then heated to 80° C. and maintained at that temperature for 2 hr. The reactor was then cooled and the reactor contents sampled. The hydrolyzable chloride content of the organic phase after the second treatment was measured and found to be further reduced to 280 ppm based on the analysis of an aliquot of the neat ACE resin product. Then, 200 g of water was added to the reactor and the reactor contents mixed for 10 min. The reactor contents were transferred to a separatory funnel. Phase separation was quick and after 30 min, 190 g of water phase was removed.

Part F: Toluene Strip

The organic phase was transferred from the funnel to the reactor and heated under vacuum in order to remove toluene. After about 3 hr of stripping operation, the reactor contents were cooled and transferred to a bottle.

Part G: Results

In this Example 1, about 270 g of final resin product was produced. The final composition of the resin product is described in Table V.

TABLE V

Composition of the Product After Toluene Strip

| CHDM-DGE (wt %) | CHDM-MGE (wt %) | Epichlorohydrin (wt %) | di(2,3-epoxypropyl) ether (wt %) | Lights plus Oligomers (wt % by difference) |
|---|---|---|---|---|
| 77.74 | 1.04 | 0.00 | 0.00 | 21.3 |

Example 2 and Comparative Example A

Using the procedure of Example 1 above, two other epoxidation experiments (Example 2 and Comparative Example A) were carried out. Example 2 and Comparative Example A were performed in which the neutralization step of each of these two examples was altered to investigate how the degree of neutralization would affect the subsequent process steps after the neutralization step, particularly what effect the degree of neutralization would have on the amount polymeric insoluble material formed during the epichlorohydrin strip step. In Example 2, the reactor contents at the end of the epoxidation reaction step were neutralized at about 20% theoretical value. In Comparative Example A, the neutralization step was omitted. The following Table VI summarizes the results:

TABLE VI

| Example | Equivalent Ratio of Epi/OH | Ratio of NaOH/OH | NaOH Addition Time (hr) | Excess NaOH Added (g) | NaH$_2$PO$_4$ Added (g, 13% solution) | Percent Neutralization (%) | Total Dried Insoluble Material Collected (g) |
|---|---|---|---|---|---|---|---|
| Example 1 | 2.5 | 1.2 | 10 | 20 | 193.7 | 84 | 1.1 |
| Example 2 | 2 | 1.2 | 7 | 22.7 | 50.1 | 20 | 1.5 |
| Comparative Example A | 2 | 1.2 | 7 | 22.8 | 0 | 0 | 18 |

The invention claimed is:

1. A process for preparing an aliphatic or cycloaliphatic epoxy resin composition comprising the steps of:
   (I) reacting a mixture of the following components:
      (a) an aliphatic or cycloaliphatic hydroxyl-containing material,
      (b) an epihalohydrin,
      (c) a stoichiometric excess of a base compound or basic acting substance,
      (d) a catalyst, and
      (e) optionally, a solvent; wherein the reacting step (I) is carried out under reaction conditions sufficient to form a crude aliphatic or cycloaliphatic epoxy resin composition product in the resultant reaction mixture;
   (II) neutralizing the resultant reaction mixture of step (I) containing the crude aliphatic or cycloaliphatic epoxy resin composition product with a phosphate neutralizing agent sufficient to partially neutralize the base or basic acting substance and to form a neutralized fluid medium containing aliphatic or cycloaliphatic epoxy resin composition product;
   (III) removing at least a portion of unreacted epihalohydrin from the reaction mixture of step (II); and
   (IV) subjecting the reaction mixture of step (III) above to a separation process to recover the aliphatic or cycloaliphatic epoxy resin composition product from the neutralized fluid medium; wherein the aliphatic or cycloaliphatic epoxy resin composition product yield is greater than about 70 percent;
   and wherein the amount of neutralizing agent used in the present process is from about 5 weight percent to about 80 weight percent of the stoichiometric excess of the base utilized during the reaction step (I).

2. The process of claim 1, wherein the aliphatic or cycloaliphatic hydroxyl containing material is cis- and trans-1,3- and 1,4-cyclohexanedimethanol; or cis and trans-1,4-cyclohexanedimethanol; and wherein the product produced is cyclohexanedimethanol epoxy resin.

3. The process of claim 1, wherein the epihalohydrin is epichlorohydrin.

4. The process of claim 1, wherein the base compound is sodium hydroxide.

5. The process of claim 1, wherein the catalyst is a non-Lewis acid catalyst.

6. The process of claim 5, wherein the non-Lewis acid catalyst is benzyltriethylammonium chloride.

7. The process of claim 1, wherein the fluid medium of the neutralizing step is water.

8. The process of claim 1, wherein the neutralizing agent is an aqueous solution of monosodium phosphate, potassium dihydrogen phosphate, phosphoric acid, and mixtures thereof.

9. The process of claim 1, wherein the neutralizing agent is an aqueous solution of sodium dihydrogen phosphate.

10. The process of claim 1, wherein the neutralizing agent is used in an amount sufficient to achieve a pH of from about 7 to about 13.

11. The process of claim 1, wherein the neutralizing agent is an aqueous solution of sodium dihydrogen phosphate; and wherein the aqueous solution contains from about 5 weight percent neutralizing agent to about 13 weight percent neutralizing agent.

12. The process of claim 1, wherein the amount of base, component (c) in step (I), is from about 1 molar equivalent to about 2 molar equivalents of base to the hydroxyl groups in the aliphatic or cycloaliphatic hydroxyl-containing material, component (a).

13. The process of claim 1, wherein the resultant reaction mixture in step (I) is neutralized sufficient to provide an amount of insoluble polymeric material in the product of less than about 10 weight percent.

14. The process of claim 1, wherein at least a portion of the unreacted epihalohydrin isolated in step (III) is recycled to step (I).

* * * * *